United States Patent
Sones et al.

(10) Patent No.: US 10,147,176 B1
(45) Date of Patent: Dec. 4, 2018

(54) AUTOMATED CONTAINER INSPECTION SYSTEM

(71) Applicant: Applied Vision Corporation, Cuyahoga Falls, OH (US)

(72) Inventors: Richard A. Sones, Cleveland Heights, OH (US); Craig A. Miller, Uniontown, OH (US)

(73) Assignee: APPLIED VISION CORPORATION, Cuyahoga Falls, OH (US)

( * ) Notice: Subject to any disclaimer, the term of this patent is extended or adjusted under 35 U.S.C. 154(b) by 132 days.

(21) Appl. No.: 15/259,007

(22) Filed: Sep. 7, 2016

(51) Int. Cl.
- *G06T 7/00* (2017.01)
- *G01N 21/952* (2006.01)
- *G06T 7/40* (2017.01)
- *H04N 5/225* (2006.01)
- *H04N 5/247* (2006.01)

(52) U.S. Cl.
CPC ......... *G06T 7/0008* (2013.01); *G01N 21/952* (2013.01); *G06T 7/408* (2013.01); *H04N 5/2256* (2013.01); *H04N 5/247* (2013.01); *G01N 2201/062* (2013.01); *G01N 2201/12* (2013.01); *G06T 2207/10024* (2013.01); *G06T 2207/30108* (2013.01); *G06T 2207/30244* (2013.01)

(58) Field of Classification Search
CPC ............. G06T 7/0008; G06T 7/408; G06T 2207/10024; G06T 2207/30108; G06T 2207/30244; G01N 21/952; G01N 2201/12; H04N 5/2256; H04N 5/247
See application file for complete search history.

(56) References Cited

U.S. PATENT DOCUMENTS

| | | | |
|---|---|---|---|
| 6,061,125 A | 5/2000 | Thomas et al. | |
| 7,271,889 B2 | 9/2007 | Cemic et al. | |
| 8,004,667 B2 | 8/2011 | Kwirandt | |
| 8,135,206 B2* | 3/2012 | Sones | G01N 21/90 382/142 |
| 8,179,434 B2* | 5/2012 | Koval | G01B 11/245 348/352 |
| 2002/0118874 A1 | 8/2002 | Chung et al. | |
| 2006/0283145 A1* | 12/2006 | Weisgerber | B07C 5/3404 53/167 |
| 2007/0237356 A1 | 10/2007 | Dwinell et al. | |
| 2012/0216689 A1 | 8/2012 | Cochran et al. | |
| 2013/0087059 A1 | 4/2013 | Baird et al. | |
| 2014/0268123 A1* | 9/2014 | Juvinall | G01N 21/9081 356/239.4 |
| 2015/0336750 A1 | 11/2015 | Coates et al. | |

* cited by examiner

*Primary Examiner* — Gregory M Desire
(74) *Attorney, Agent, or Firm* — Medley, Behrens & Lewis, LLC

(57) ABSTRACT

Described herein are various technologies pertaining to automated container inspection. A region in an image of a container is labeled as being subject to depicting reflections. When determining whether or not the container is defective based upon the image of the container, values of pixels of the image are compared to corresponding statistics of such pixels, where the statistics can identify an acceptable distribution of values for a pixel. For pixels in the above-mentioned region, more variance in the values of the pixels is allowed (compared to allowed variance when analyzing values of pixels outside of the region) when determining whether or not the container is defective based upon the values of the pixels.

20 Claims, 10 Drawing Sheets

AUTOMATED CONTAINER INSPECTION SYSTEM

BACKGROUND

Production plants for manufacturing containers (such as beverage cans) can produce a very large number of containers, with sophisticated (multicolor) decoration thereon, in a relatively short amount of time. For instance, a conventional decorator in a container production plant can decorate 2,000 containers per minute. Container decorations have intrinsic value, as consumers tend to attach perceptions of quality of a product based upon the design on the container that holds the product.

Conventionally, there is a lack of robust inspection of exterior surfaces of containers at these container production plants. A known process for container inspection is tasking an operator at the plant with periodically pulling containers from a conveyor for visual inspection. For instance, every so often (e.g., every 15 minutes), the operator may be tasked with pulling a small number of containers off of the conveyor and visually inspecting the containers to ensure that the exterior surfaces of the containers are free of readily apparent defects (e.g., to ensure that proper colors are applied to the exterior surfaces of the containers, to ensure that the exterior surfaces of the containers are free of smears, etc.). Using this conventional approach, thousands of defective containers may be manufactured prior to the operator noticing a defect on the exterior surface of one or more of the sampled containers. In practice, these (completed) containers must be scrapped, resulting in significant cost to the container manufacturer.

Recently, automated systems have been developed and deployed in container production plants, wherein such systems are configured, through automated visual inspection, to detect defects on exterior surfaces of containers. These systems include multiple cameras that are positioned to capture images of an exterior surface of a container when the conveyor passes through an inspection region. The images captured by the cameras are then analyzed to determine whether the exterior surface of the container includes a defect. Many containers, such as aluminum beverage containers, however, have mirror-like qualities, rendering it difficult for automated inspection systems to differentiate between a reflected image (which is not a defect in the container) and an actual defect, such as a smear. More specifically, light that illuminates the exterior surfaces of a container may reflect off of numerous surfaces (including surfaces of adjacent containers on a conveyor that transports the containers through the inspection region), which causes reflections of portions of the adjacent containers to appear in images of the exterior surfaces of the container under inspection. Additionally, light can accentuate minor defects (that are tolerable to industry standards) on the external surfaces of containers. These reflections and accentuated minor defects render it difficult for an automated inspection system to distinguish among: 1) a reflection in an otherwise defect-free container; 2) an accentuated minor defect; and 3) a container that includes a defect.

SUMMARY

The following is a brief summary of subject matter that is described in greater detail herein. This summary is not intended to be limiting as to the scope of the claims.

Described herein is a container inspection system that is configured to ascertain whether a container being transported on a conveyor includes a defect on an exterior surface of the container. The container inspection system can detect various defects on exterior surfaces of containers, including physical defects, such as dents, creases, etc. Additionally, the container inspection system can detect defects that may occur in a design or label on an exterior surface of a container, such as an improper color being printed on the container (e.g., a color shade is incorrect), smearing, and so forth, such that the design or label does not appear as desired. The container inspection system includes a light source that is configured to emit light that illuminates the container. In an example, the light source can include a light emitting diode (LED) or other suitable source of light. The container inspection system includes several cameras that are configured to simultaneously generate images of the exterior surface of the sidewall of the container while such surface is being illuminated by the light source. More specifically, the light source is strobed, such that the aforementioned container surface is illuminated for a relatively short amount of time (e.g., on the order of tens of microseconds). The cameras capture respective images of the exterior surface of the sidewall of the container while such surface is being illuminated. The container, though rapidly moving, appears motionless in the images of the exterior surface of the sidewall of the container because of the simultaneous strobing of the light source and capturing of the images.

The container inspection system also includes a computing system that is in communication with the cameras, wherein the computing system is configured to, for each container passing through the inspection region: 1) receive images of an external surface of a sidewall of a container generated by the cameras; 2) identify regions in each image based upon positions of the cameras relative to the container when the images were captured; 3) create an unwrapped image of the container at least partially by stitching the images of the container generated by the cameras together, while maintaining the identified regions in the unwrapped image; 4) perform a first type of processing for pixels of the unwrapped image that are within the regions, while performing a second type of processing for pixels of the unwrapped image that are outside the regions; and 5) output an indication as to whether or not the container is defective based upon the first and second type of processing.

More specifically, the unwrapped image includes several pixels that have respective values, and the computing system can compare the unwrapped image to a statistical model of a non-defective container (e.g., where the statistical model includes pixels and corresponding value distributions). The computing system, when comparing the unwrapped image with the statistical model, can allow for more variance between values of pixels in the identified regions and corresponding values of pixels in the statistical model when compared to the allowed variance between values of pixels outside the identified regions and corresponding values of pixels in the statistical model. In other words, since the identified regions are known (based on geometries of the inspection system and containers passing through the inspection region) to include reflections or accentuate "scuffs", pixels in these regions in the unwrapped image can be compared to corresponding pixels in corresponding regions in the statistical model with less precision relative to the precision used when comparing pixels outside these regions in the unwrapped image to corresponding pixels in the statistical model.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
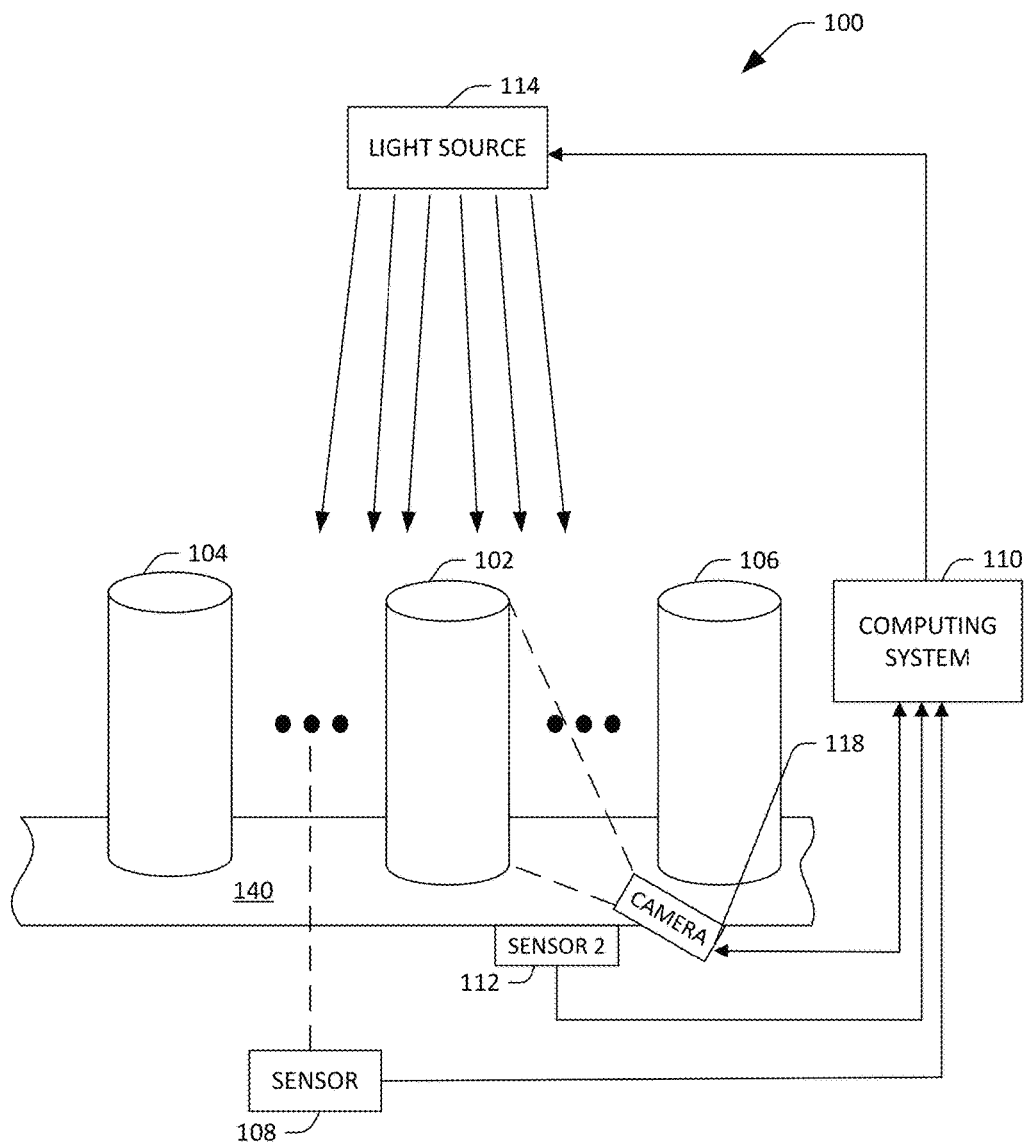
FIG. 1 is a schematic of an exemplary container inspection system.

Various technologies pertaining to a container inspection system are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Further, as used herein, the term "exemplary" is intended to mean serving as an illustration or example of something, and is not intended to indicate a preference.

Described herein are features relating to container inspection, where such features are well-suited to reduce a number of containers incorrectly identified as being defective by an automatic container inspection system (compared to conventional inspection systems). Summarily, at least one region in an image of a container being inspected can be identified, wherein such region is known to include reflections and/or "scuffs". A computing system, when analyzing the image, can compare a value of a pixel in the image with a statistical model of the pixel (which is indicative of, for instance, acceptable values of the pixel). The computing system can perform the aforementioned comparison differently depending upon whether or not the pixel resides in the identified region. For instance, the computing system may require a more precise alignment between the pixel value and the statistical model of the pixel when the pixel is outside the identified region compared to when the pixel is inside the identified region. Additional detail is set forth below.

With reference now to FIG. 1, an exemplary container inspection 100 is illustrated. Generally, the container inspection system 100 is configured to inspect exterior surfaces of sidewalls of containers 102-104 for defects as the containers 102-104 are transported by a conveyor 140 through an inspection region of the container inspection system 100. In an example, the container inspection system 100 can be configured to detect functional defects in one or more of the containers 102-104, such as dents, creases, malformations in shape of one or more of the containers 102-104, etc. Further, the container inspection system 100 can be configured to detect defects in text and/or graphics printed on the exterior surfaces of the sidewalls of the containers 102-104. For instance, the container inspection system 100 can be configured to detect that the container 102 has a design printed thereon that includes an improper color (or an insufficient amount of a color). In another example, the container inspection system 100 can be configured to detect that text on a label applied to the exterior surface of the sidewall of the container 102 is smudged.

Once the container inspection system 100 identifies that a container has a defect on the exterior surface of the sidewall thereof, the container inspection system 100 can cause the defective container to be removed from the conveyor 140, such that it is not populated with a product (e.g., beverage), and therefore does not reach the hands of an end consumer. Further, the container inspection system 100 can be configured to analyze containers at a relatively high rate of speed, such as on the order of 1,000 containers per minute to 6,000 containers per minute. Moreover, the container inspection system 100 can be configured to detect defects in containers of various shapes and/or sizes. Thus, while the containers 102-104 are shown as being cylindrical, the container inspection system 100 is not limited to detecting defects in cylindrical containers. Rather, the container inspection system can be configured to detect defects in elongated cubic containers, elongated ellipsoidal containers, conical containers, etc.

The container inspection system 100 optionally includes a first sensor 108 that is configured to output a signal that indicates that a container has reached a particular position relative to an inspection region of the container inspection system 100. For instance, the first sensor 108 may be an optical sensor that receives an optical beam from an optical transmitter. When a container transported by the conveyor 140 breaks the optical beam, the sensor 108 can output a signal that indicates that the optical beam has been interrupted, and thus the container has reached the certain position.

The container inspection system 100 further includes a computing system 110 that is in communication with the first sensor 108 and receives the signal output by the first sensor 108. The container inspection system 100 can further optionally include a second sensor 112 that is configured to monitor movement of the conveyor 140. For example, the second sensor 112 can be a rotary encoder coupled to a pulley that is attached to the conveyor 140, wherein the second sensor 112 outputs signals based upon rotation of the pulley. The computing system 110 is in communication with the second sensor 112, and receives signals output by the second sensor 112. The computing system 110, then, can ascertain position of a container relative to the first sensor 108 (and thus relative to the inspection region of the system 100) based upon signals output by the sensors 108 and 112.

The container inspection system 100 also includes a light source 114 that is in communication with the computing system 110, wherein the computing system 110 controls operation of the light source 114 based upon signals output by the sensors 108 and 112. More specifically, the computing system 110 causes the light source 114 to flash when a container is at a certain position relative to the light source 114 (such that the light source 114 strobes as the conveyor 140 transports containers). The light source 114 can be a light emitting diode, a plurality of light emitting diodes arranged in a ring, a matrix of light emitting diodes, etc.

While the system 100 is shown as including one light source, it is to be understood that the system 100 can include two, four, six, eight, or more light sources, such that an entirety of the exterior surface of the sidewall of the container 102 is illuminated by light emitted from the light sources.

The container inspection system 100 further includes a camera 118 that is in communication with the computing system 110 and is controlled by the computing system 110. More particularly, the computing system 110 causes the camera 118 to capture an image of the exterior surface of the sidewall of the container 102 while the exterior surface is being illuminated by way of the light source 114. In other words, the camera 118 generates an image of the exterior surface of the sidewall of the container 102 when such surface is illuminated. The camera 118 then provides the image to the computing system 110, and the computing system 110 generates an indication as to whether or not the container 102 is defective based upon the image generated by the camera 118. While the container inspection system 100 is illustrated as including a single camera, it is to be understood that, in operation, the container inspection system 100 can include multiple cameras 118 positioned around the container 102 when the container is in the inspection region (e.g., when the exterior sidewall of the container is illuminated by the light emitted from the light source 114). For instance, the container inspection system 100 can include three cameras, four cameras, or more, such that the cameras generate images encompassing an entirety of an exterior surface of the sidewall of the container 102.

The computing system 110 receives the images of the container 102 generated by the plurality of cameras and, in an example where the container 102 is cylindrical, unwraps the cylinder using image processing techniques to create an unwrapped image. The computing system 110 may then align the unwrapped image with a statistical model of an unwrapped cylinder that represents a container that is free of defects. This alignment places the unwrapped image in pixel-by-pixel correspondence with the statistical model of the unwrapped cylinder. Thereafter, the computing system 110 compares the unwrapped image with the statistical model—if there is sufficient similarity between the unwrapped image and the statistical model, then the computing system 110 can output an indication that the container 102 is free of defects. Conversely, if the computing system 110 compares the unwrapped image with the statistical model and identifies a sufficient dissimilarity therebetween, the computing system 110 can output an indication that the container 102 is defective, and cause the container 102 to be removed from the conveyor 140.

In an embodiment, the computing system 110 generates the statistical model based upon images of a number of non-defective containers. The container inspection system 100, prior to inspecting containers, processes a preselected number of non-defective containers. With more specificity, the camera 118 captures images of non-defective containers as such containers pass through the inspection region of the system 100. The computing system 110 forms unwrapped images of these containers as described above, and aligns the unwrapped images with one another. During alignment, the computing system 110 can perform any suitable image processing technique to create a pixel-by-pixel correspondence between unwrapped images, where each pixel has a value assigned thereto, with the value being indicative of color of the pixel. Using these pixel values, the computing system 110 can form a statistical model of a container that is to be inspected, where the statistical model includes, for instance, a distribution of values for each pixel.

In another embodiment, the statistical model can be determined a priori, based upon known ideal pixel values and acceptable deviations from such pixel values.

In an embodiment, as mentioned previously, the computing system 110 compares the unwrapped image with the statistical model on a pixel-by-pixel basis. The computing system 110 receives a value for each pixel in the unwrapped image. The computing system 110 then compares the value with statistics for the corresponding pixel in the statistical model. Based upon comparisons between values of pixels in the unwrapped image of the container with the statistics of corresponding pixels in the statistical model, the computing system can output an indication as to whether or not the container is defective.

In conventional automated container inspection systems, each pixel in an unwrapped image of a container is analyzed in the same manner when comparing each pixel in the unwrapped image with a corresponding pixel in the statistical model. In contrast to conventional systems, the container inspection system 100 takes into consideration geometry of containers as well as positions of cameras relative to containers when performing the above-described comparison, such that the computing system 110 compares different pixels in an unwrapped image with corresponding pixels in the statistical model differently, depending upon whether or not such pixels are in a region of an image known to correspond to reflection and/or accentuated (non-defective) features. Additional explanation is below.

Containers being inspected by the container inspection system 100 are often manufactured of reflective material, such as aluminum, steel, or the like. Even when containers are painted, reflections can appear on exterior surfaces of the containers, and such reflections are then captured in images of the containers. These reflections exist in certain regions of images, where a location of a region in an image in which a reflection exists depends upon geometries of the system: a location of the container 102 relative to the camera 118 when the camera 118 captures an image, a location of an adjacent container (e.g., the container 106) on the conveyor 140 relative to the container 102 when the camera 118 captures the image, etc.

A container inspected by the container inspection system 100 may also include non-defective features, such as "scuffs". A scuff is a minor abrasion in paint on the exterior surface of a container, which may often be imperceptible to the human eye unless high intensity light impacts the container at the abrasion and the abrasion is viewed from a shallow viewing angle. Similar to the reflections discussed above, a scuff will be perceivable only in certain regions of images. Thus, when the container 102 is undergoing inspection, a scuff on the container 102, when the location of the scuff is included in an image captured by the camera 118, will only be perceivable in a certain region of the image. The location of this region in the image is based upon geometries of the container inspection system 100, such as location of the light source 114 relative to the container 102 when the camera 118 captures the image, location of the container 102 relative to the camera 118 when the camera captures the image, orientation of the camera 118 relative to the container 102 when the camera 118 captures the image, etc.

Since the geometries of the container inspection system 100 are relatively static (with the possible exception of distance between containers being somewhat variable), the above-described regions can be relatively static across images captured by the camera 118. For instance, the regions can be vertical bands in the image. The computing system 110 can assign a label to each pixel in an image captured by the camera 118, where a label assigned to a pixel indicates whether or not the pixel is within a region (band). The label can further optionally indicate whether the pixel is within a region corresponding to reflections or a region corresponding to accentuated (non-defective) features, such as scuffs.

Responsive to the label(s) being assigned to the pixels in the image, the computing system 110 can create an unwrapped image of the container 102, where the unwrapped image of the container 102 is based upon multiple images captured by multiple cameras positioned around the inspection region of the container inspection system 100. The computing system 110 can be configured to create the unwrapped image using any suitable image processing technique, where images captured by multiple cameras may be subject to warping and stitching to form the unwrapped image. The computing system 110 retains the regions in the unwrapped image, such that the unwrapped image includes at least one region (band) for each image used to form the unwrapped image. Thus, when the container inspection system 100 includes four cameras, the unwrapped image of the container 102 includes at least four bands (and possibly eight bands): first bands corresponding to reflection; and second bands corresponding to minor abrasions.

The computing system 110 can thereafter align the unwrapped image with a statistical model of a container, while retaining the bands. Therefore, conceptually, if the computing system 110 shifts the unwrapped image to the left to align the unwrapped image with the statistical model, then the bands are likewise shifted to the left. The computing system 110 then compares values of pixels in the unwrapped image to statistics of corresponding pixels in the statistical model. For instance, the statistical model can comprise a plurality of pixels, and each pixel can have a distribution assigned thereto, where the distribution is indicative of values of the pixel that correspond to a non-defective container. The computing system 110 can compare the value of each pixel with the corresponding statistics in the statistical model, and can output an indication as to whether or not the container 102 is defective based upon such comparison. For instance, if values of the pixels of the unwrapped image correspond to the statistics in the statistical model, the computing system 110 can output an indication that the container 102 is not defective. Contrarily, if values of the pixels of the unwrapped image do not correspond to the statistics in the statistical model, the computing system 110 can output an indication that the container 102 is defective.

In contrast to conventional approaches, the computing system 110 takes into consideration whether or not a pixel is within one of the bands when determining whether or not the container 102 is defective. More specifically, as noted above, a band in the unwrapped image is a region where reflections may exist; and it is desirable to prevent the computing system 110 from improperly identifying a reflection on the exterior surface of the container 102 as being a defect. Accordingly, the computing system 110 can be configured such that the computing system 110 is less sensitive to potential defects within the bands when compared to how sensitive the computing system 100 is to potential defects outside the bands.

In a non-limiting example, the computing system 110 can be configured with a first sensitivity threshold when comparing pixels outside of the band with corresponding statistics in the statistical model, and can be configured with a second sensitivity threshold when comparing pixels within the band with corresponding statistics in the statistical model. For example, for a particular pixel in the statistical model, the average value can be 10. When a pixel in the unwrapped image that corresponds to the particular pixel is outside of a band, the computing system 110 is configured with the first sensitivity threshold, which may indicate that the value for the particular pixel should be within two of the average value (e.g., between 8 and 12). When the pixel in the unwrapped image is within a band, the computing system 110 is configured with the second sensitivity threshold, which may indicate that the value for the particular pixel should be within five of the average value (e.g., between 5 and 15). Again, since the bands are susceptible to depicting scuffs and/or reflections, the computing system 110 can be configured to be less sensitive to potential defects when comparing values of pixels in the bands with corresponding statistics in the statistical model.

Figure 2:
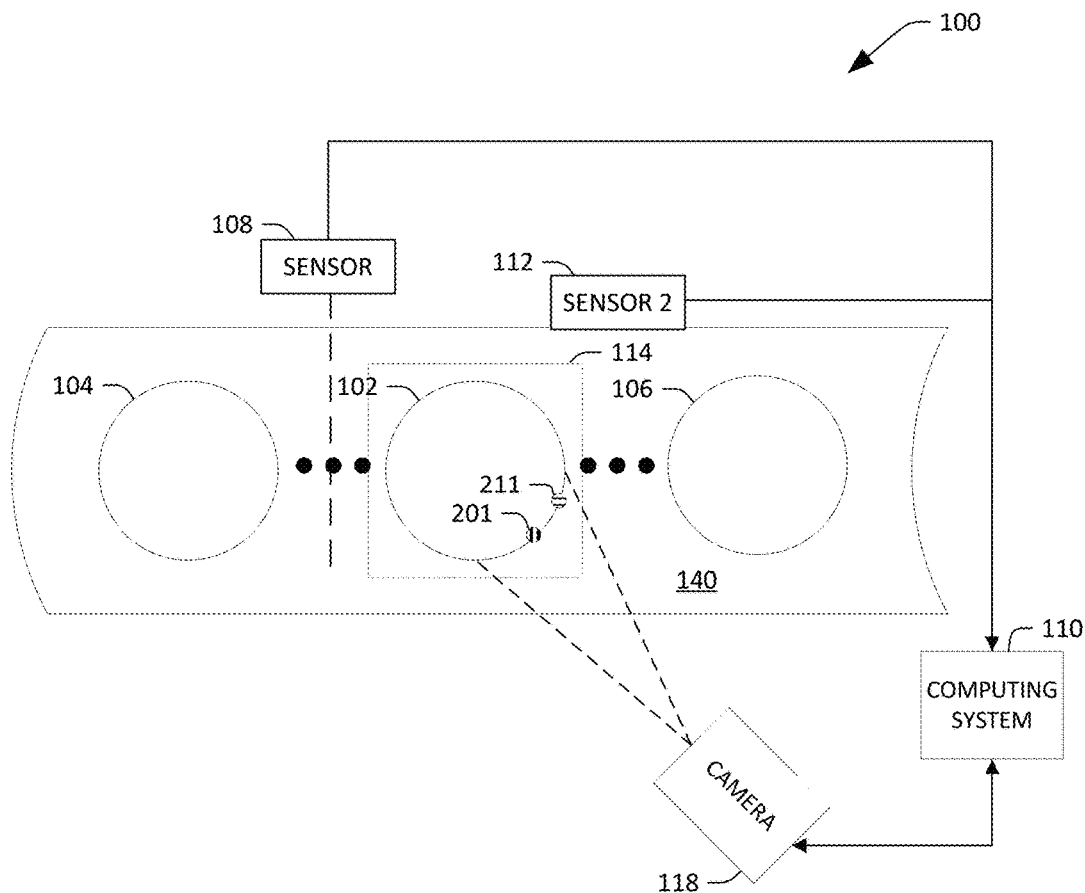
FIG. 2 is a top-down view of an exemplary container inspection system.

Turning now to FIG. 2, a top-down view of the container inspection system 100 is illustrated. Due to the spatial arrangement of the camera 118 relative to the container 102, there exists an area 201 in the field of view of the camera 118 where reflections of an adjacent container 106 appear in an image taken by the camera 118 when the container 102 is within the inspection region. This area corresponds to a band, as noted above.

Additionally, the size of the area 201 is related to the distance between the container 102 and the adjacent container 106 on the conveyor 140. As a distance between the container 102 and the first adjacent container 106 decreases, the size of the area 201 increases. Conversely, as a distance between the container 102 and the first adjacent container 106 increases, the size of the area 201 decreases. The computing system 110 can be configured to receive information indicative of a distance between the container 102 and the adjacent container 106 (e.g., from the first sensor 108 and the second sensor 112). Based upon this information, the computing system 110 can alter the width of the band in the image captured by the camera 118 (such that the width of the band is a function of the distance between the container 102 and the adjacent container 106). It is to be understood that containers are placed on the conveyor 140 and moved through the inspection system 100 at relatively high speed; accordingly, distance between containers may not be uniform.

Additionally, the intensity of the reflection of the adjacent container 106 in the area 201 may further be affected by the distance between the container 102 and the adjacent container 106, such that as a distance between the container 102 and the adjacent container decreases, intensity of a reflection of the adjacent container 106 in the container increases. The computing system 110 can adjust the sensitivity threshold when comparing values of pixels in the band with corresponding statistics in the statistical model.

Additionally, the reflective properties of the container 102 may affect the intensity of the reflections of the adjacent container 106 that exist in the container 102. When the container 102 is formed of a material or painted with a paint that has a high reflectance, more intense reflections of the adjacent container 106 appear in the image of the container 102 captured by the camera 118 (and thus also appear in the unwrapped image). Conversely, when the container 102 is formed of a material or painted with a paint that has a low reflectance, less intense reflections of the adjacent container 106 appear in the image of the container 102 captured by the camera 118. The computing system 110 can be configured to receive information regarding the reflectance of containers for an inspection session. The computing system 110, then, can be further configured to adjust the sensitivity threshold with respect to pixels in the band as a function of reflectance.

Moreover, as noted previously, the container 102 may have non-defective features (scuffs) that may be accentuated in an image of the exterior surface of the container 102 captured by the camera 118. Due to geometries of the system 100, these features are accentuated in an image captured by the camera 118 when they exist in a second area 211 of the container 102. The computing system 118 can define a band in images captured by the camera 118, where the band encompasses a region in the images where the features noted above are accentuated. As noted previously, the computing system 118 can use a different sensitivity threshold when comparing pixels of an unwrapped image within the band with corresponding statistics of a statistical model when compared to the sensitivity threshold used when comparing pixels of the unwrapped image outside the band with corresponding statistics of the statistical model.

Figure 3:
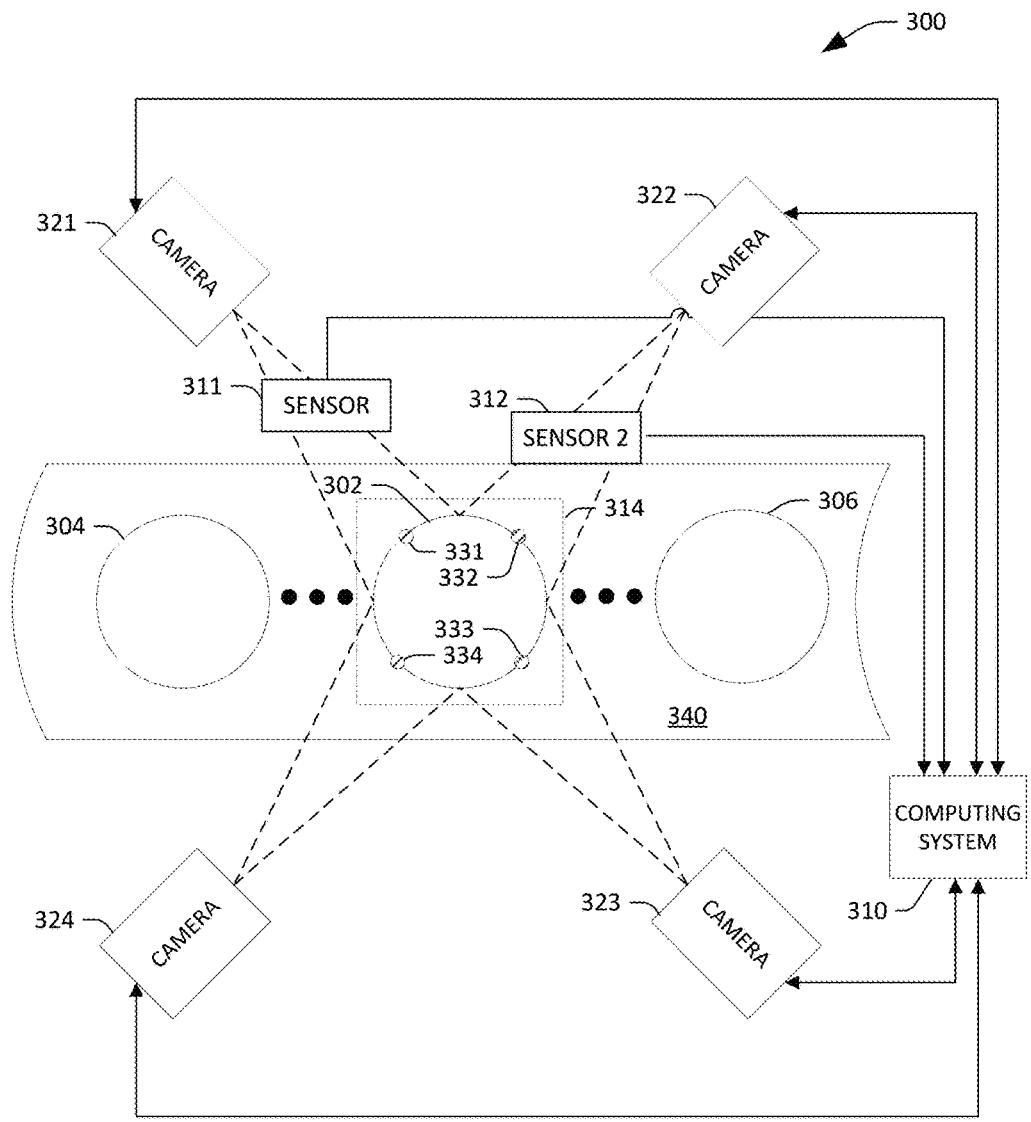
FIG. 3 is a top-down view of an exemplary container inspection system that includes four cameras.

With reference to FIG. 3, a top-down view of an exemplary container inspection system 300 that includes four cameras 321-324 is illustrated. The container inspection system 300 is configured to inspect exterior surfaces of sidewalls of containers 302-306 for defects as the containers 302-306 are transported by a conveyor 340 through an inspection region of the container inspection system 300. For each of the four cameras, a respective area 331-334 includes reflection(s) of a first adjacent container 304 and/or a second adjacent container 306. There also exists areas (not shown) that are known to correspond to non-defective features that are accentuated in images captured by the cameras.

The computing system 310, in communication with the cameras 321-324, causes the cameras 321-324 to simultaneously capture images of the exterior surface of the sidewall of the container 302 while the exterior surface is being illuminated by way of the light source 314. The computing system 310 receives the images, and further receives data that is indicative of distances between: 1) the container 302 and a first adjacent container 304; and 2) the container 302 and a second adjacent container 306.

The computing system 310, in an example where the container 302 is cylindrical, assigns labels to pixels in the images captured by the cameras 321-324, where the labels indicate whether or not the pixels are within one of the bands (e.g., a band corresponding to reflections or a band corresponding to accentuated non-defective features). The computing system 310 subsequently creates an unwrapped image of the cylinder from images of the container 302 captured by the cameras 321-324 using image processing techniques, while retaining the labels noted above.

The computing system 310 then aligns the unwrapped image with the statistical model, and compares values of pixels in the aligned, unwrapped image with the statistical model as described above (e.g., using different sensitivity thresholds).

Figure 4:
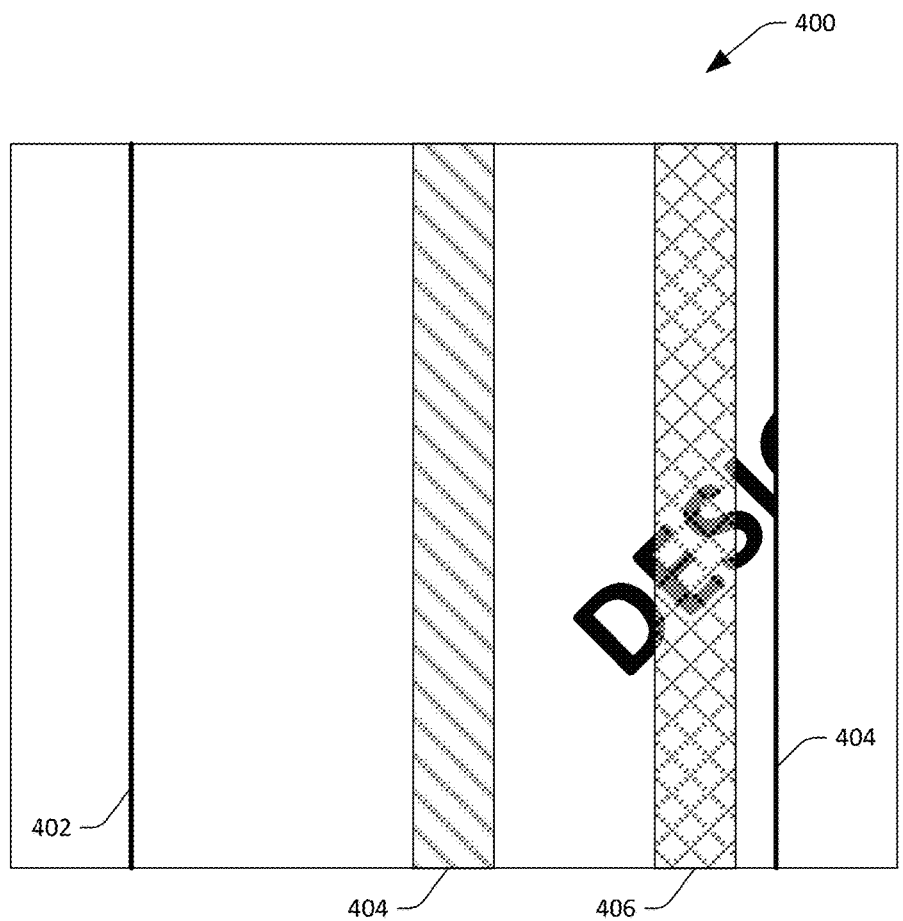
FIG. 4 depicts an image captured by a camera of a container inspection system.
Figure 5:
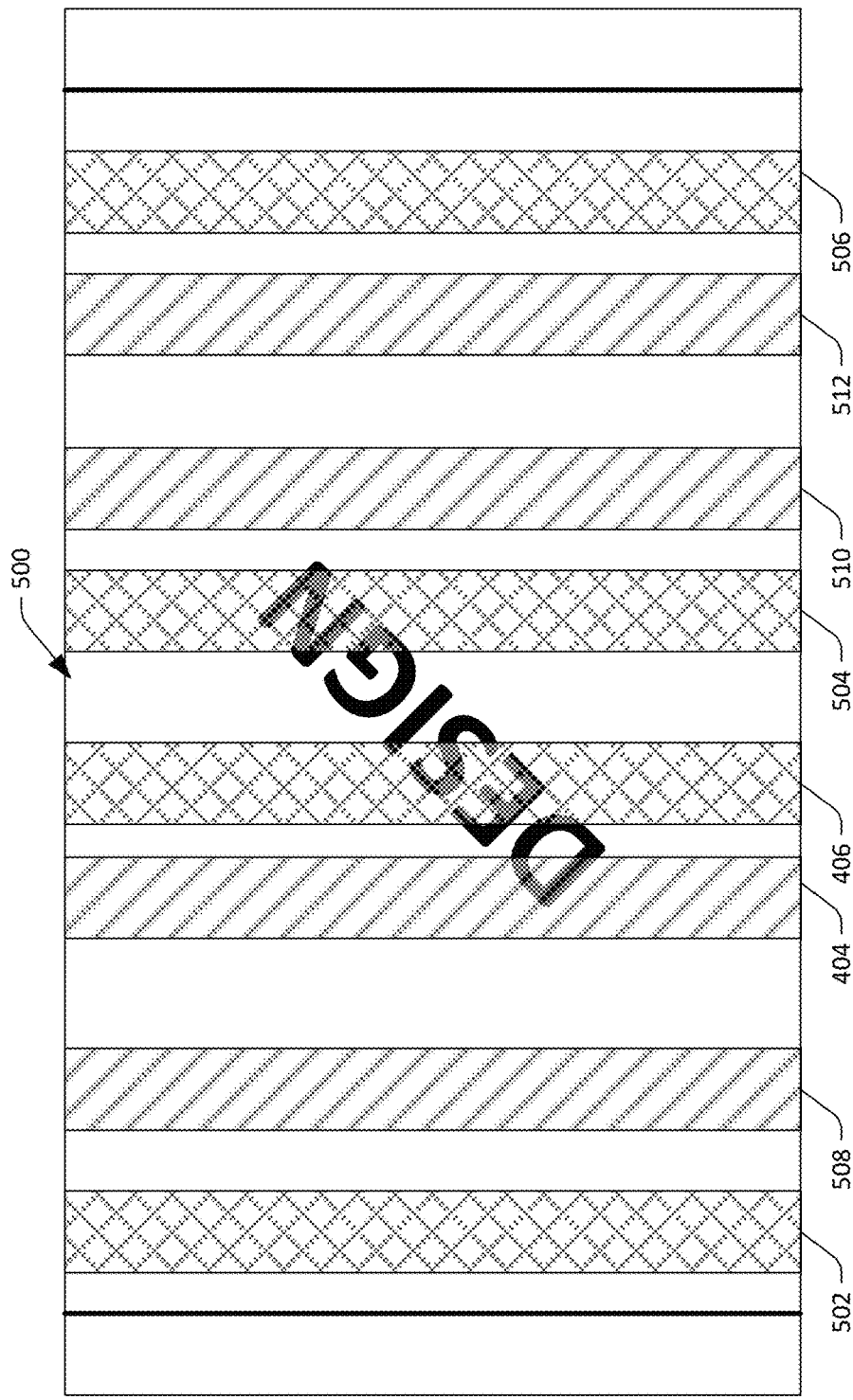
FIG. 5 depicts an image of an unwrapped container (an unwrapped image), where the unwrapped image is formed based upon the image shown in FIG. 4.
Figure 6:
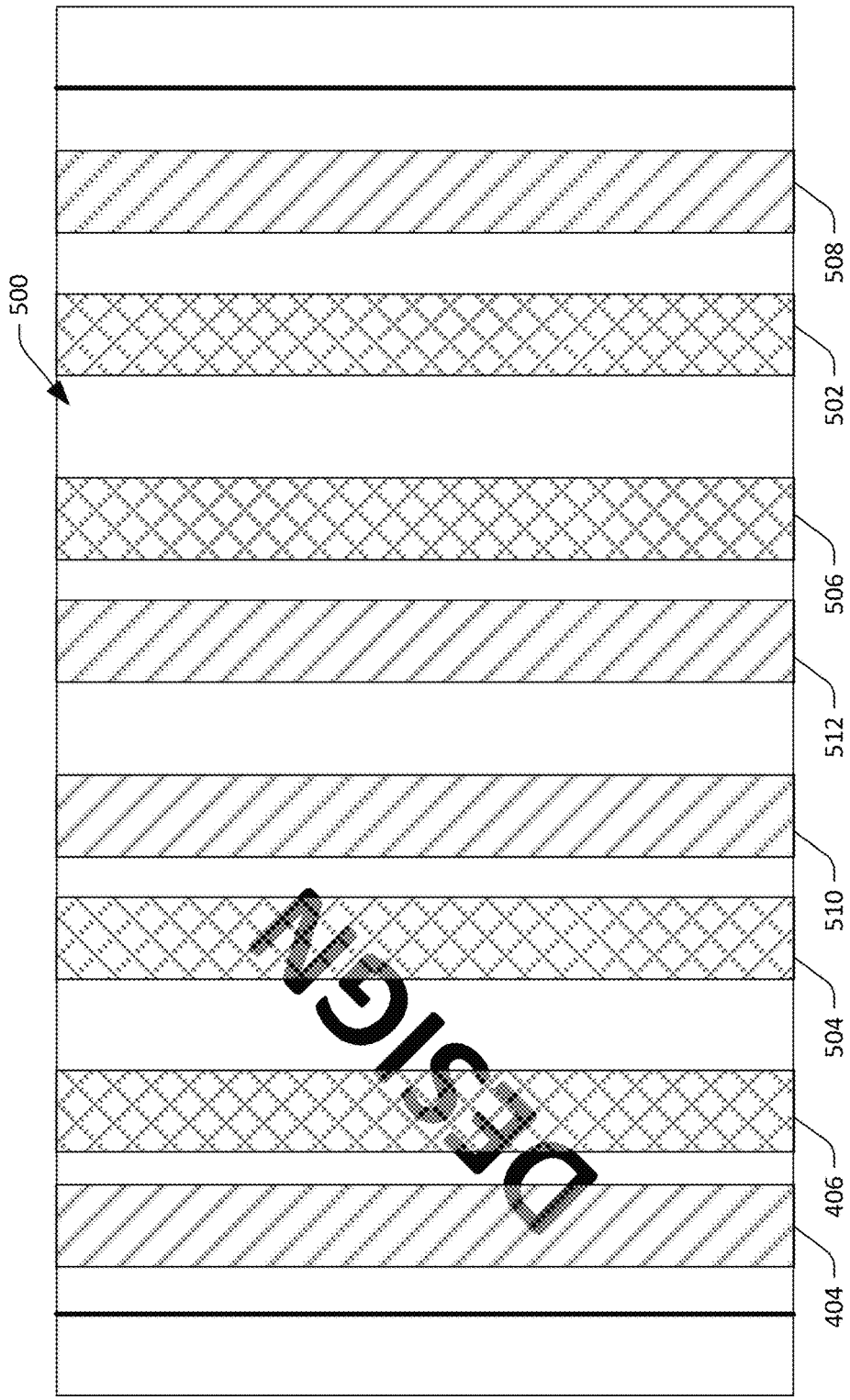
FIG. 6 depicts the unwrapped image subsequent to the unwrapped image being aligned with a statistical model.

FIGS. 4-6 depict a sequence of images that are set forth to illustrate operation of the computing system 310 when the computing system determines whether or not a container is defective. In an example, the container 302 undergoing inspection may be a cylindrical container formed of a metal (such as aluminum), with a design depicted thereon (the word "DESIGN" slanting upwards). The portion of the container where "DESIGN" is depicted may be unpainted or painted in a highly reflective color, such as silver, while the remainder of the container may be printed with a less reflective color (such as red).

With reference now solely to FIG. 4, an image 400 captured, for instance, by the camera 323 when the container 302 is within the examination region of the container inspection system 300 is illustrated. The image 400 captures a portion of the exterior surface of the sidewall of the container 302, where lines 402 and 404 depict boundaries of the container 302 as captured in the image 400. The image 400 includes a portion of the word "DESIGN". The computing system 310 can define bands 404 and 406 in the image 400, where each pixel in the band 404 is labeled to indicate that the pixel corresponds to a region in the image 400 where non-defective features (such as scuffs) are accentuated, and further where each pixel in the band 406 is labeled to indicate that the pixel corresponds to a region in the image 400 where reflections are captured in the image. Pixels not included in the bands 404 and 406 can also be labeled to indicate that such pixels are not in a band.

Now referring to FIG. 5, an exemplary unwrapped image 500 of the container 302 is depicted. The unwrapped image 500 is constructed based upon the image 400 as well as images captured by cameras 321, 322, and 324 when the container 302 is in the inspection region of the container inspection system 300. The unwrapped image 500 includes the bands 404 and 406, which are carried over from the image 400. The unwrapped image also includes bands 502, 504, and 506, where pixels in the bands 502-506 are labeled to indicate that such pixels correspond to a region in the image 500 where reflections are existent. The unwrapped image 500 further comprises bands 508, 510, and 512, where pixels in the bands 508-512 are labeled to indicate that such pixels correspond to a region in the image 500 where non-defective features may be accentuated. As noted previously, while the bands are depicted as being rectangular, it is to be understood that the bands may have other shapes, where the shape can depend upon geometries of the container inspection system 300 (e.g., tilt of the cameras 321-324 relative to the sidewall of containers being inspected, distance between the cameras 321-324 and the sidewall of containers, position of the light source, and so forth.

Now referring to FIG. 6, the unwrapped image 500 is depicted subsequent to the computing system 310 aligning the unwrapped image 500 with the statistical model. Compared to the unwrapped image 500 as shown in FIG. 5, the unwrapped image has been shifted to the left, such that the "DESIGN" text is closer to the left side of the image 500. The computing system 310 aligns the unwrapped image 500 with the statistical model so that a pixel-by-pixel comparison can be undertaken between the unwrapped image 500 and corresponding statistics of the statistical model. It is to be noted that the bands 404, 406, and 502-512 are also shifted in the unwrapped image 500 shown in FIG. 6.

Figure 7:
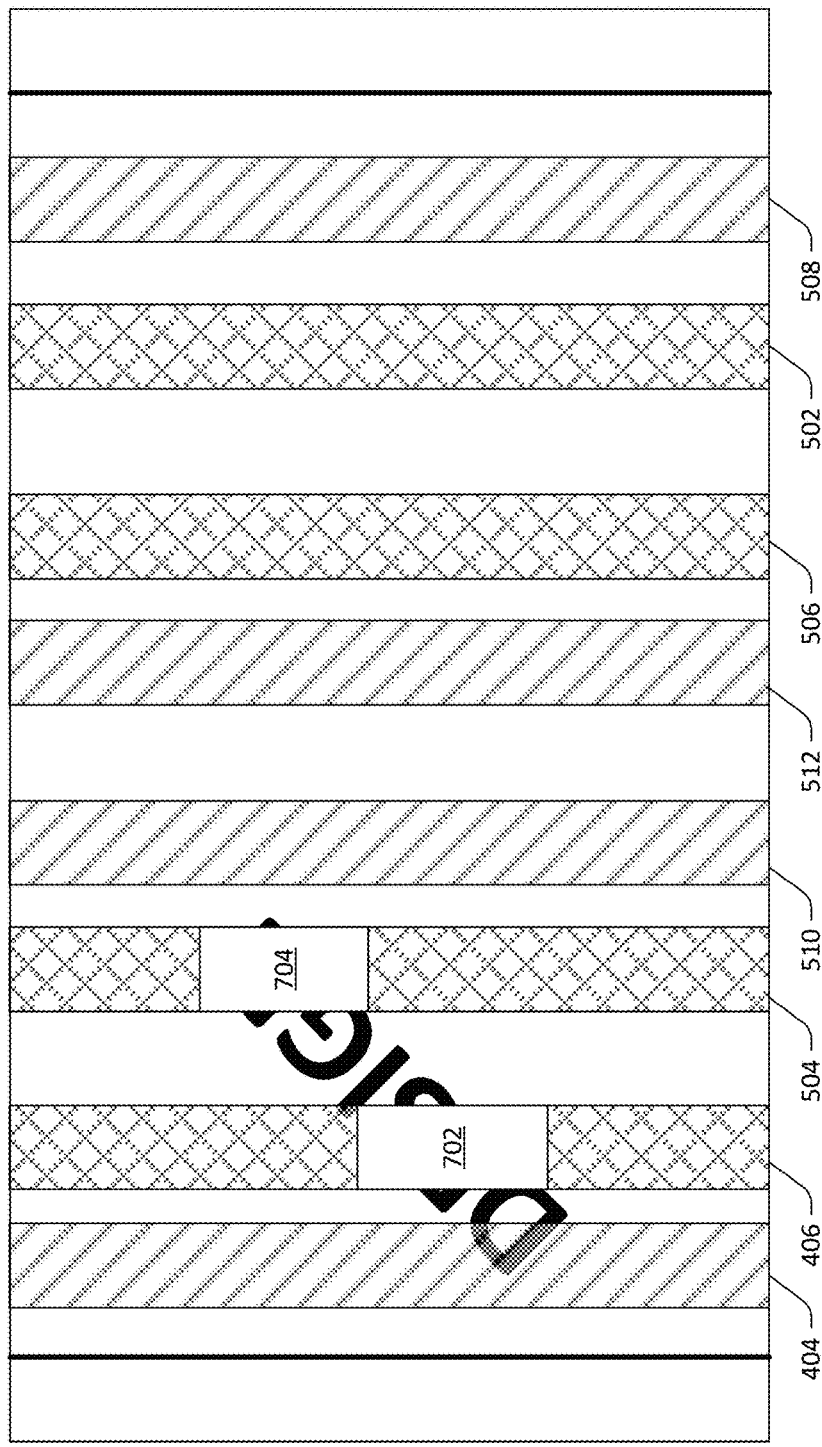
FIG. 7 depicts the aligned, unwrapped image with masks assigned thereto.

Turning now to FIG. 7, the aligned, unwrapped image 500 is depicted, where additional masks are placed in portions of some of the bands. More specifically, the image 500 includes a first mask 702 in the band 406, and a second mask 704 in the band 504. As noted previously, the word "DESIGN" on the container is highly reflective, and the bands 406 and 504 are regions in the unwrapped image 500 where reflections are subject to appearing. Accordingly, the computing system 310 can place the masks 702 and 704 in the bands 406 and 504, respectively, where pixels beneath the masks 702 and 702 can be assigned labels that indicate that such pixels are highly subject to depicting reflections. Thus, when the computing system 310 compares values of pixels in the unwrapped, aligned, and masked image 500, the computing system 310 can employ several different sensitivity thresholds: 1) a first sensitivity threshold for pixels not within a band, where less variance is tolerated between values of such pixels and corresponding statistics of the statistical model; 2) a second sensitivity threshold for pixels in the bands 404 and 508-512, where more variance is tolerated between values of such pixels and corresponding statistics of the statistical model compared to the first sensitivity threshold, such that accentuated non-defective features are not improperly identified as defects; 3) a third sensitivity threshold for pixels in the bands 402 and 502-506 (but not under the masks 702 and 704), where more variance is tolerated between values of such pixels and corresponding statistics of the statistical model compared to the first sensitivity threshold; and 4) a fourth sensitivity threshold for pixels in the masks 702 and 704, where more variance is tolerated between values of such pixels and corresponding statistics of the statistical model when compared to the third sensitivity threshold.

Figure 8:
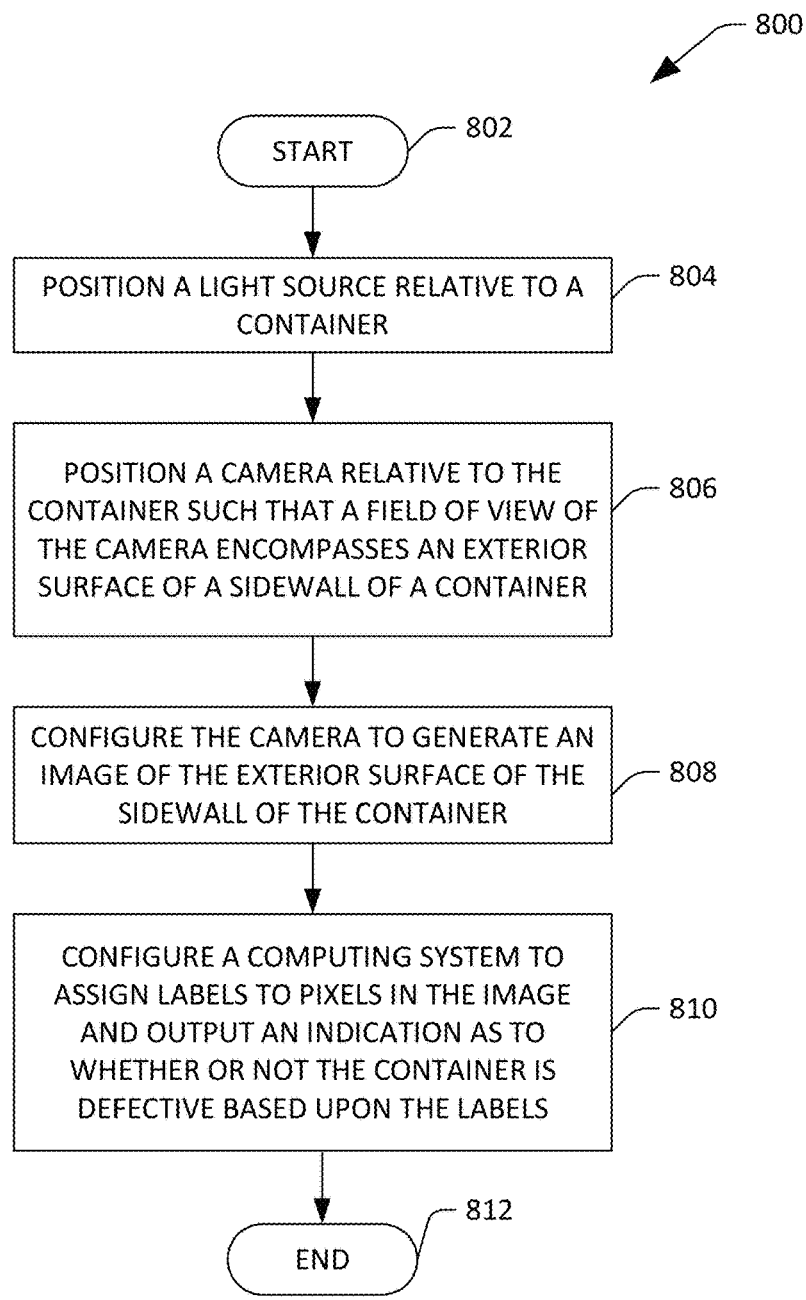
FIG. 8 is a flow diagram illustrating an exemplary methodology for configuring a container inspection system.
Figure 9:
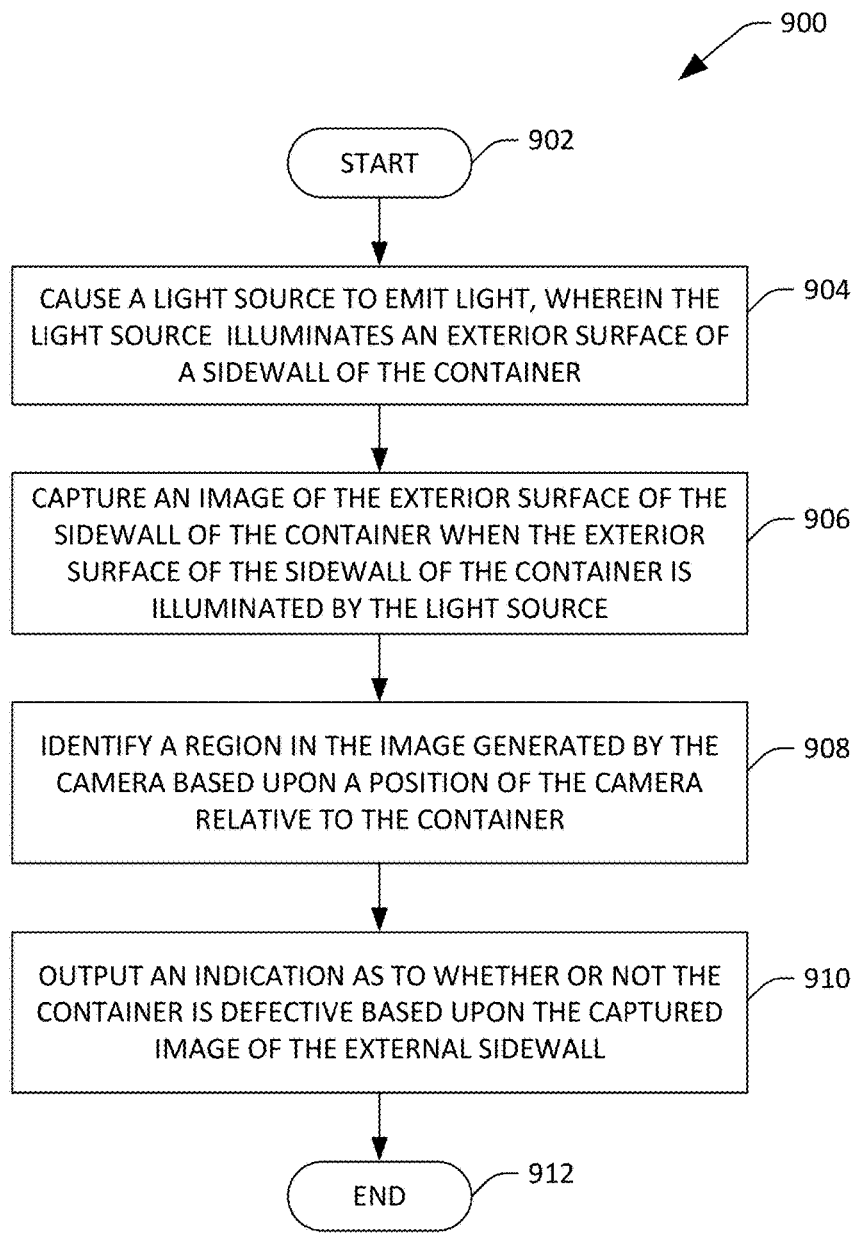
FIG. 9 is a flow diagram illustrating an exemplary methodology for operating a container inspection system.

FIGS. 8-9 illustrate exemplary methodologies relating to configuring and operating a container inspection system. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Now referring to FIG. 8, an exemplary methodology 800 for configuring a container inspection system is illustrated. The methodology 800 starts at 802, and at 804 a light source is positioned relative to an inspection region, such that the light emitted by the light source will illuminate an exterior surface of a sidewall of a container that passes through the inspection region.

At 806, a camera is positioned relative to the inspection region, such that a field of view of the camera encompasses the exterior surface of the sidewall of the container when the external surface is illuminated by the light source. The camera is configured to capture an image of the exterior surface of the sidewall of the container when the container is being transported by a conveyor through the inspection region of the container inspection system.

At 808, the camera is configured to generate an image of the exterior surface of the sidewall of the container when the exterior surface of the sidewall of the container is illuminated by the tapering field of light.

At 810, the computing system is configured to: receive the image generated by the camera; label pixels in the image, where the labels are indicative of whether or not the pixels are within a band that corresponds to reflections that are to be suppressed; and generate an indication as to whether or not the container is defective based upon the labels assigned to the pixels. The methodology 800 completes at 812.

Referring now to FIG. 9, an exemplary methodology 900 that facilitates operating a container inspection system is illustrated. The methodology 900 starts at 902, and at 904, a light source is caused to emit light that illuminates an exterior surface of a sidewall of the container. As described previously, this is performed while the container is being transported at a relatively high rate of speed along a conveyor.

At 906, an image of the exterior surface of the sidewall of the container is captured while the exterior service of the sidewall of the container is illuminated by the light source. At 908, a region in the image is labeled as corresponding to potentially unwanted reflections and/or accentuated non-defective features based upon a position of the camera relative to the container. At 910, this image is analyzed and an indication is output as to whether or not the container is defective based upon the image and the labeled region of the image. The methodology 900 completes at 912.

Figure 10:
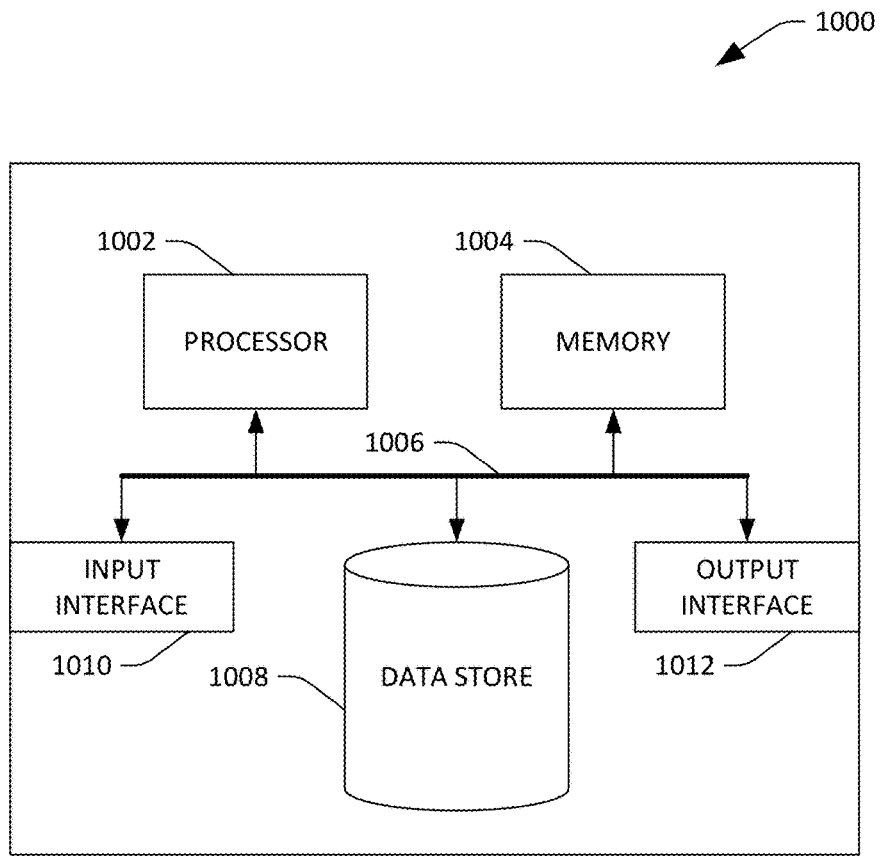
FIG. 10 is an exemplary computing device.

Referring now to FIG. 10, a high-level illustration of an exemplary computing device 1000 that can be included in the computing system 110 is illustrated. The computing device 1000 includes at least one processor 1002 that executes instructions that are stored in a memory 1004. The instructions may be, for instance, instructions for implementing functionality described as being carried out by the computing system 110, as described above. The processor 1002 may access the memory 1004 by way of a system bus 1006. In addition to storing executable instructions, the memory 1004 may also store images, threshold values, etc.

The computing device 1000 additionally includes a data store 1008 that is accessible by the processor 1002 by way of the system bus 1006. The data store 1008 may include executable instructions, images, etc. The computing device 1000 also includes an input interface 1010 that allows external devices to communicate with the computing device 1000. For instance, the input interface 1010 may be used to receive instructions from an external computer device, from a user, etc. The computing device 1000 also includes an output interface 1012 that interfaces the computing device 1000 with one or more external devices. For example, the computing device 1000 may display text, images, etc. by way of the output interface 1012.

It is contemplated that the external devices that communicate with the computing device 1000 via the input interface 1010 and the output interface 1012 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1000 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1000 may be a distributed system. Thus, for instance, several devices may be in communication by way of a network connection and may collectively perform tasks described as being performed by the computing device 1000.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A container inspection system comprising:
    a light source configured to illuminate an exterior surface of a sidewall of a container when the container is in an inspection region of the container inspection system;
    a camera configured to generate an image of the exterior surface of the sidewall of the container when the exterior surface is illuminated by the light source; and
    a computing system in communication with the camera, the computing system configured to perform acts comprising:
        receiving the image generated by the camera;
        assigning labels to pixels in the image generated by the camera, wherein the labels are assigned based upon a position of the camera relative to the container when the image of the container was generated by the camera, wherein the labels comprise first labels and second labels, wherein the first labels indicate that pixels of the image that have been assigned the first labels are subject to depicting reflections in the exterior surface of the sidewall of the container, and wherein the second labels indicate that pixels of the image that have been assigned the second labels are subject to depicting accentuated abrasions in paint applied to the exterior surface of the sidewall of the container;
        determining whether or not the container is defective based upon the labels assigned to the pixels; and
        responsive to determining whether or not the container is defective, outputting an indication as to whether or not the container is defective.

2. The container inspection system of claim 1, wherein the first labels are assigned to pixels in a band of the image that extends along a height of the image.

3. The container inspection system of claim 1, wherein determining whether or not the container is defective comprises:
    generating an unwrapped image of the container based upon multiple images of the container, the multiple images of the container captured simultaneously, the multiple images of the container comprise the image of the container, wherein the labels are assigned to pixels in the unwrapped image of the container.

4. The container inspection system of claim 3, wherein determining whether or not the container is defective further comprises:
    aligning the unwrapped image of the container with a statistical model, the statistical model being a model of non-defective containers, wherein the statistical model comprises statistics that correspond to pixels of the unwrapped image, and wherein the labels are maintained when the unwrapped image is aligned with the statistical model;
    comparing values of pixels in the unwrapped image with corresponding statistics in the statistical model; and
    determining whether or not the container is defective based upon the comparing of values of the pixels in the unwrapped image with the corresponding statistics in the statistical model.

5. The container inspection system of claim 4, wherein the labels are assigned to pixels in a band of the image that extends along a height of the image, and wherein determining whether or not the container is defective further comprises:
employing a first sensitivity threshold when comparing the values of the pixels in the band with corresponding statics in the statistical model; and
employing a second sensitivity threshold when comparing values of pixels outside the band with corresponding statistics in the statistical model.

6. The container inspection system of claim 3, wherein the unwrapped image comprises multiple bands, each band corresponding to a different image from the multiple cameras.

7. The container inspection system of claim 1, wherein the labels are assigned to the pixels based upon data that is indicative of a distance between the container and an adjacent container on a conveyor that transports the container and the adjacent conveyor through the inspection region.

8. The container inspection system of claim 1, wherein a subset of the first labels indicate that pixels to which the subset of labels are assigned have reflectance that is greater than pixels to which other labels in the first labels are assigned.

9. The container inspection system of claim 1, wherein assigning the labels to the pixels in the image generated by the camera comprises:
determining a width of a band in the image based upon data that is indicative of a distance between the container and an adjacent container on a conveyor that transports containers through the inspection region; and
assigning the labels to pixels in the band, the labels indicating that the pixels in the band are subject to including reflections in the container.

10. A method executed by a computing device of a container inspection system, the method comprising:
receiving, from a camera, an image of an exterior surface of a sidewall of a container, wherein the camera captures the image as the container is transported through an inspection region of the inspection system by a conveyor;
responsive to receiving the image, assigning a band to the image, wherein location of the band in the image is based upon a position of the camera relative to the container when the camera captured the image, and wherein assigning the band to the image comprises labeling pixels in the band with labels that indicate that the pixels are inside the band;
determining whether or not the container is defective based upon values of the pixels in the band, wherein determining whether or not the container is defective based upon the values of the pixels in the band comprises:
determining whether the values of the pixels in the band are within a first specified variance of corresponding statistics of a statistical model of a container; and
determining whether values of pixels outside the band are within a second specified variance of corresponding statistics of the statistical model of the container, where the first specified variance is different from the second specified variance; and
outputting an indication as to whether or not the container is defective responsive to determining whether or not the container is defective.

11. The method of claim 10, wherein the container is cylindrical and formed of a metal.

12. The method of claim 10, further comprising:
receiving data that is indicative of a distance between the container and a second container on the conveyor; and
assigning the band to the image based upon the data that is indicative of the distance.

13. The method of claim 10, wherein the band extends vertically through the image.

14. The method of claim 10, further comprising:
responsive to assigning the band to the image, forming an unwrapped image of the container, wherein the unwrapped image of the container is formed based upon the image and a plurality of other images simultaneously captured with the image by a plurality of other cameras, wherein the unwrapped image of the container comprises the band.

15. The method of claim 14, wherein the unwrapped image of the container comprises at least four bands assigned to the unwrapped image by the computing device.

16. The method of claim 10, wherein the statistical model comprises pixels that correspond to pixels in the unwrapped image, and further comprises statistics for each pixel in the statistical model, where the statistics include a distribution of values for each pixel.

17. The method of claim 10, wherein the labels assigned to the pixels indicate that the portion of the image in the band is one of:
subject to depicting reflections in the container; or
subject to depicting accentuations of non-defective features.

18. A computer-readable storage medium comprising instructions that, when executed by at least one processor, cause the at least one processor to perform acts comprising:
generating an unwrapped image of a cylindrical container based upon a plurality of images of the cylindrical container captured simultaneously by a plurality of cameras, the plurality of images captured as the cylindrical container passes through an inspection region of a container inspection system on a conveyor, wherein the unwrapped image comprises a region that includes a plurality of pixels, and where each pixel in the plurality of pixels is assigned a label that indicates that each pixel in the plurality of pixels is subject to depicting reflections in the container, and further wherein a location of the region in the unwrapped image is based upon a position of a camera in the plurality of cameras relative to the cylindrical container when the camera captured an image of the cylindrical container;
determining whether or not the container is defective based upon whether values of the plurality of pixels in the region are within a first specified variance of corresponding statistics of a statistical model of a container;
determining whether or not the container is defective based upon whether values of pixels outside the region are within a second specified variance of corresponding statistics of the statistical model of the container, where the first specified variance is different from the second specified variance;
when the container is determined to be defective, causing the container to be removed from the conveyor.

19. The computer-readable storage medium of claim 18, the acts further comprising:
receiving data that is indicative of a distance between the cylindrical container and a second cylindrical container on the conveyor; and
determining the region of the image based upon the data that is indicative of the distance, wherein the labels are assigned to the plurality of pixels subsequent to the region of the image being determined.

20. The computer-readable storage medium of claim 18, wherein the unwrapped image comprises a second region that has a second plurality of pixels, wherein each pixel in the second plurality of pixels is assigned a label that indicates that the second region is subject to depicting accentuated abrasions in paint applied to the exterior surface of the sidewall of the cylindrical container.

* * * * *